US008295567B2

(12) United States Patent  (10) Patent No.: US 8,295,567 B2
Watson et al.  (45) Date of Patent: Oct. 23, 2012

(54) SYSTEMS AND METHODS FOR RIDGE SELECTION IN SCALOGRAMS OF SIGNALS

(75) Inventors: James Watson, Dunfermline (GB); Paul Stanley Addison, Edinburgh (GB); David Clifton, Midlothian (GB)

(73) Assignee: Nellcor Puritan Bennett Ireland, Mervue, Galway (IE)

( * ) Notice: Subject to any disclaimer, the term of this patent is extended or adjusted under 35 U.S.C. 154(b) by 879 days.

(21) Appl. No.: 12/245,326

(22) Filed: Oct. 3, 2008

(65) Prior Publication Data

US 2009/0324034 A1  Dec. 31, 2009

Related U.S. Application Data

(60) Provisional application No. 61/077,029, filed on Jun. 30, 2008, provisional application No. 61/077,130, filed on Jun. 30, 2008.

(51) Int. Cl.
*G06K 9/00* (2006.01)

(52) U.S. Cl. ........ 382/128; 382/207; 381/94.1; 600/323; 607/7

(58) Field of Classification Search .................. 382/128, 382/207; 381/94.1; 600/323; 607/7
See application file for complete search history.

(56) References Cited

U.S. PATENT DOCUMENTS

| | | |
|---|---|---|
| 4,289,141 A | 9/1981 | Cormier |
| 5,285,783 A | 2/1994 | Secker |
| 5,291,884 A | 3/1994 | Heinemann et al. |
| 5,431,170 A | 7/1995 | Mathews |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,916,154 A | 6/1999 | Hobbs et al. |
| 5,967,995 A | 10/1999 | Shusterman et al. |
| 6,002,952 A | 12/1999 | Diab et al. |
| 6,011,985 A | 1/2000 | Athan et al. |
| 6,036,653 A | 3/2000 | Baba et al. |
| 6,094,592 A | 7/2000 | Yorkey et al. |
| 6,095,984 A | 8/2000 | Amano et al. |

(Continued)

FOREIGN PATENT DOCUMENTS

JP  4332536  11/1992

(Continued)

OTHER PUBLICATIONS

Addison, Paul S., The Illustrated Wavelet Transform Handbook, Taylor & Francis Group, 2002.
Addison, Paul, "The Little Wave with the Big Future," Physics World, Mar. 2004, pp. 35-39.
Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

(Continued)

*Primary Examiner* — Long Pham

(57) ABSTRACT

According to embodiments, systems, devices, and methods for ridge selection in scalograms are disclosed. Ridges or ridge components are features within a scalogram which may be computed from a signal such as a physiological (e.g., photoplethysmographic) signal. Ridges may be identified from one or more scalograms of the signal. Parameters characterizing these ridges may be determined. Based at least in part on these parameters, a ridge density distribution function is determined. A ridge is selected from analyzing this ridge density distribution function. In some embodiments, the selected ridge is used to determine a physiological parameter such as respiration rate.

17 Claims, 16 Drawing Sheets
(3 of 16 Drawing Sheet(s) Filed in Color)

U.S. PATENT DOCUMENTS

| | | | |
|---|---|---|---|
| 6,117,075 A | 9/2000 | Barnea |
| 6,129,675 A | 10/2000 | Jay |
| 6,135,966 A | 10/2000 | Ko |
| 6,151,518 A | 11/2000 | Hayashi |
| 6,163,715 A | 12/2000 | Larsen et al. |
| 6,171,257 B1 | 1/2001 | Weil et al. |
| 6,171,258 B1 | 1/2001 | Karakasoglu et al. |
| 6,181,958 B1 | 1/2001 | Steuer et al. |
| 6,208,951 B1 | 3/2001 | Kumar et al. |
| 6,217,523 B1 | 4/2001 | Amano et al. |
| 6,293,915 B1 | 9/2001 | Amano et al. |
| 6,325,761 B1 | 12/2001 | Jay |
| 6,352,502 B1 | 3/2002 | Chaiken et al. |
| 6,361,501 B1 | 3/2002 | Amano et al. |
| 6,393,311 B1 | 5/2002 | Edgar, Jr. et al. |
| 6,415,166 B1 | 7/2002 | Van Hoy et al. |
| 6,453,184 B1 | 9/2002 | Hyogo et al. |
| 6,510,331 B1 | 1/2003 | Williams et al. |
| 6,516,209 B2 | 2/2003 | Cheng et al. |
| 6,526,301 B2 | 2/2003 | Larsen et al. |
| 6,553,242 B1 | 4/2003 | Sarussi |
| 6,561,986 B2 | 5/2003 | Baura et al. |
| 6,608,934 B2 | 8/2003 | Scheirer et al. |
| 6,654,622 B1 | 11/2003 | Eberhard et al. |
| 6,654,623 B1 | 11/2003 | Kastle |
| 6,709,402 B2 | 3/2004 | Dekker |
| 6,748,252 B2 | 6/2004 | Lynn et al. |
| 6,760,610 B2 | 7/2004 | Tschupp et al. |
| 6,773,397 B2 | 8/2004 | Kelly |
| 6,810,277 B2 | 10/2004 | Edgar, Jr. et al. |
| 6,909,912 B2 | 6/2005 | Melker |
| 6,931,269 B2 | 8/2005 | Terry |
| 6,985,762 B2 | 1/2006 | Brashears et al. |
| 7,001,337 B2 | 2/2006 | Dekker |
| 7,020,507 B2 | 3/2006 | Scharf et al. |
| 7,035,679 B2 | 4/2006 | Addison et al. |
| 7,043,293 B1 | 5/2006 | Baura |
| 7,054,453 B2 | 5/2006 | Causevic et al. |
| 7,054,454 B2 | 5/2006 | Causevic et al. |
| 7,079,888 B2 | 7/2006 | Oung et al. |
| 7,171,269 B1 | 1/2007 | Addison et al. |
| 7,173,525 B2 | 2/2007 | Albert |
| 7,203,267 B2 | 4/2007 | De Man et al. |
| 7,209,775 B2 | 4/2007 | Bae et al. |
| 7,222,054 B2 | 5/2007 | Geva |
| 7,225,013 B2 | 5/2007 | Geva et al. |
| 7,254,432 B2 | 8/2007 | Fine |
| 7,254,500 B2 | 8/2007 | Makeig et al. |
| 7,289,835 B2 | 10/2007 | Mansfield et al. |
| 7,309,314 B2 | 12/2007 | Grant et al. |
| 7,341,560 B2 | 3/2008 | Henderson et al. |
| 7,349,727 B2 | 3/2008 | Obata et al. |
| 7,353,054 B2 | 4/2008 | Kawasaki et al. |
| 7,387,607 B2 | 6/2008 | Holt et al. |
| 7,398,115 B2 | 7/2008 | Lynn |
| 7,431,696 B1 | 10/2008 | Brady et al. |
| 7,515,949 B2 | 4/2009 | Norris |
| 7,519,488 B2 | 4/2009 | Fu et al. |
| 7,523,011 B2 | 4/2009 | Akiyama et al. |
| 2001/0051767 A1 | 12/2001 | Williams et al. |
| 2003/0163057 A1 | 8/2003 | Flick et al. |
| 2005/0043616 A1 | 2/2005 | Chinchoy |
| 2005/0070774 A1* | 3/2005 | Addison et al. ............... 600/323 |
| 2005/0085735 A1 | 4/2005 | Baker et al. |
| 2005/0119708 A1 | 6/2005 | Haefner |
| 2005/0192493 A1 | 9/2005 | Wuori |
| 2005/0197552 A1 | 9/2005 | Baker |
| 2005/0267346 A1 | 12/2005 | Faber et al. |
| 2006/0058595 A1 | 3/2006 | Herrmann |
| 2006/0092029 A1 | 5/2006 | Browne et al. |
| 2006/0155206 A1 | 7/2006 | Lynn |
| 2006/0189880 A1 | 8/2006 | Lynn et al. |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2006/0276697 A1 | 12/2006 | Demuth et al. |
| 2007/0021673 A1 | 1/2007 | Arbel et al. |
| 2007/0027368 A1 | 2/2007 | Collins et al. |
| 2007/0073120 A1 | 3/2007 | Li et al. |
| 2007/0073124 A1 | 3/2007 | Li et al. |
| 2007/0083097 A1 | 4/2007 | Fujiwara et al. |
| 2007/0118028 A1 | 5/2007 | Kitajima et al. |
| 2007/0129647 A1 | 6/2007 | Lynn |
| 2007/0142719 A1 | 6/2007 | Kawasaki et al. |
| 2007/0167694 A1 | 7/2007 | Causevic et al. |
| 2007/0167851 A1 | 7/2007 | Vitali et al. |
| 2007/0213621 A1 | 9/2007 | Reisfeld et al. |
| 2007/0213622 A1 | 9/2007 | Reisfeld |
| 2007/0219439 A1 | 9/2007 | Vilser et al. |
| 2007/0282212 A1 | 12/2007 | Sierra et al. |
| 2007/0299323 A1 | 12/2007 | Arns et al. |
| 2008/0045832 A1 | 2/2008 | McGrath |
| 2008/0076992 A1 | 3/2008 | Hete et al. |
| 2008/0077026 A1 | 3/2008 | Banet et al. |
| 2008/0082018 A1 | 4/2008 | Sackner et al. |
| 2008/0146901 A1 | 6/2008 | Katura et al. |
| 2008/0188733 A1 | 8/2008 | Al-Ali et al. |
| 2008/0200775 A1 | 8/2008 | Lynn |
| 2008/0214903 A1 | 9/2008 | Orbach |
| 2008/0243021 A1 | 10/2008 | Causevic et al. |
| 2008/0262326 A1 | 10/2008 | Hete et al. |
| 2008/0296514 A1 | 12/2008 | Metzger et al. |

FOREIGN PATENT DOCUMENTS

| | | |
|---|---|---|
| JP | 2004135854 | 5/2004 |
| JP | 2004194908 | 7/2004 |
| JP | 2004261364 | 9/2004 |
| JP | 3825459 | 4/2005 |
| JP | 2006158974 | 6/2006 |
| JP | 2007267761 | 10/2007 |
| JP | 2007319247 | 12/2007 |
| JP | 2008110108 | 5/2008 |
| JP | 2008161657 | 7/2008 |
| WO | WO-9111137 | 8/1991 |
| WO | WO-0125802 | 4/2001 |
| WO | WO-0162152 | 8/2001 |
| WO | WO-03000125 | 1/2003 |
| WO | WO-03039326 | 5/2003 |
| WO | WO-03055395 | 7/2003 |
| WO | WO-2004075746 | 9/2004 |
| WO | WO-2004105601 | 12/2004 |
| WO | WO-2005009221 | 2/2005 |
| WO | WO-2005064314 | 7/2005 |
| WO | WO-2005096170 | 10/2005 |
| WO | WO-2006085120 | 8/2006 |
| WO | WO-2006100685 | 9/2006 |
| WO | WO-2007048989 | 5/2007 |

OTHER PUBLICATIONS

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

* cited by examiner

SYSTEMS AND METHODS FOR RIDGE SELECTION IN SCALOGRAMS OF SIGNALS

CROSS-REFERENCE TO RELATED APPLICATIONS

This claims the benefit of U.S. Provisional Application Nos. 61/077,029 entitled "Systems and Methods for Ridge Selection in Scalograms of Signals" and 61/077,130 entitled "Systems and Methods of Signal Processing," both filed Jun. 30, 2008, which are hereby incorporated by reference herein in their entireties.

SUMMARY

The present disclosure relates to signal processing and, more particularly, the present disclosure relates to using continuous wavelet transforms for processing, for example, a photoplethysmograph (PPG) signal.

The present disclosure may be used in connection with any signal having one or more repetitive components, including, for example, biosignals (e.g., a photoplethysmograph (PPG) signal, electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof. When one or more scalograms are generated from such signals using a continuous wavelet transform, repetitive components of the signals may create one or more ridges at a given scale. These ridges within the scalograms may be useful in identifying such repetitive characteristics. For example, scalograms for PPG signals include a ridge at the scale corresponding to a subject's pulse (such ridges are often referred to as the "pulse band"). Some repetitive characteristics may not form a clean ridge within the scalogram for a variety of reasons. For example, noise may drown-out or break-up a repetitive component, or environmental factors (e.g., sensor position) may affect the quality of the sensed signal. As yet another example, the wavelet employed may accentuate or de-accentuate various characteristics of a signal. One type of wavelet may result in a clearly defined ridge for the repetitive component, but another may not.

The present disclosure also relates to methods for selecting a ridge in a scalogram of a signal, the method comprising transforming the signal using a wavelet transform to generate a transformed signal, generating a first wavelet scalogram based at least in part on the transformed signal, detecting ridges within a region of the first wavelet scalogram, determining one or more parameters for the detected ridges, determining a ridge density distribution function based at least in part on the one or more parameters, and selecting a ridge having the scale corresponding to the maximum value of the ridge density distribution function. In some embodiments, the signal is a photoplesthymographic signal. In some embodiments, the method further comprises filtering the first wavelet scalogram. Optionally, the method further comprises generating a second wavelet scalogram based at least in part on a signal derived from the first wavelet scalogram and detecting ridges within a region of the second wavelet scalogram.

In some embodiments, the parameters of the detected ridges are selected from the group consisting of ridge power, ridge energy, ridge energy density, ridge amplitude variability, ridge scale variability, ridge consistency, intrinsic scale, ridge length, maximum ridge amplitude, standard deviation of intrinsic scale, standard deviation of amplitude, mean scale, median scale, mean amplitude, median amplitude, or strength-length product. In other embodiments, the method further comprises determining a physiological parameter based on the selected ridge. In some embodiments, this physiological parameter is respiration rate.

In some embodiments, ridges may be identified within the scalograms using any suitable approach. In some embodiments, the ridges themselves may be identified using local maxima. Points not identified as local maxima may be zeroed out or ignored. The local maxima may be analyzed to determine, for example, points located with in a predetermined area of each other to identify points that make up the ridges. Broken ridges may be connected by interpolating between adjacent ridges. Broken ridges may be identified by looking for the end of one ridge that is within a predefined distance/space/area (time, scale, and amplitude) of the beginning of another ridge. Ridge parameters may be determined in a number of different ways. In many instances, ridges may be defined by an array of points, thus allowing for ridge parameterization. Ridges that fall within certain ranges of scales (e.g., those outside the range of scales expected to contain the repetitive characteristic) may be ignored or deleted based on filtering and/or other techniques.

In some embodiments, ridges may be characterized at least in part using any suitable set of parameters. For example, ridge power, ridge energy, ridge energy density, ridge amplitude variability, ridge scale variability, ridge consistency, intrinsic scale, ridge length, maximum ridge amplitude, standard deviation of intrinsic scale, median scale, median amplitude, strength-length product (e.g., multiplying the maximum, mean, or median strength of all or a portion of a ridge against the total length (or any other portion) of the ridge), standard deviation of amplitude, mean scale, median scale, mean amplitude, median amplitude, or any other suitable characterizing parameter may be determined.

In some embodiments, the computation or derivation of the ridge characterizing parameters may be based at least in part on any suitable quantities, e.g., ridge length, maximum amplitude, standard deviation of the scale over a predetermined time window, standard deviation of the amplitude at a predetermined scale, mean or median scale, mean or median amplitude, or a strength-length product, or any other suitable quantities. In some embodiments, the strength-length product is computed by multiplying the maximum strength of a ridge by the length of the ridge. In some embodiments, the strength-length product is computed by multiplying the mean strength of a ridge by the length of the ridge. In other embodiments, the strength-length product is computed by multiplying the median strength of a ridge by the length of the ridge. According to some embodiments, the strength-length of a ridge may be computed using the parameters of the entire ridge or only portions thereof.

In some embodiments, the ridge density distribution function for one or more ridges may be determined by a weighted average of the ridge parameters of these ridges. The ridge density distribution function for a ridge may also be determined from a single ridge parameter, e.g., strength or strength-length product. The ridge density distribution function for one or more ridges may be determined using coefficients and weightings. In some embodiments, ridges may be weighted based at least in part on the calculated/derived parameters of the ridges. Certain parameters may be considered more important than others in the weighting applied in a ridge density distribution function. For example, the strength, length or strength-length of a ridge may be considered a more important parameter than other parameters. Other parameters may decrease the weighting of a ridge in the ridge density distribution function such as variability of parameters along the ridge such as amplitude and scale variation.

In one embodiment, the signal is a PPG signal and the desired, repetitive characteristic is the subject's respiration (for determining, e.g., the subject's respiration rate). One or more scalograms may be generated from the PPG signal. The one or more scalograms may include, for example, a primary scalogram of the original PPG signal, and secondary scalograms generated using secondary waveform feature decoupling (SWFD) applied to the pulse band within the primary scalogram. Ridges in the scale-range of expected respiration rates (e.g., rates below the pulse ridge) are identified in each of the scalograms. Parameters of these ridges are determined such that ridge power, energy, energy density, variability, consistency, intrinsic scale, length, or any other suitable characterizing features may be computed or derived. A ridge density distribution as a function of scale is calculated, determining the density of ridges as a function of scale, and the optimal scale is selected for determining the respiration rate. The optimal scale may be the scale having the highest ridge density based at least in part on the one or more ridge parameters.

The present disclosure also relates to a device for determining a physiological parameter, the device comprising a sensor for measuring a physiological signal, and a processor capable of receiving the measured physiological signal from the sensor, transforming the signal using a wavelet transform to generate a transformed signal, generate a first wavelet scalogram based at least in part on the transformed signal, detecting ridges within a region of the first wavelet scalogram, determine one or more parameters for the detected ridges, determining a ridge density distribution function based at least in part on the one or more parameters, and selecting a ridge having the scale corresponding to the maximum value of the ridge density distribution function. Optionally, the device may contain a display for displaying the determined physiological parameter.

In an embodiment the disclosure relates to a computer-readable medium comprising computer-executable instructions which, when executed by a processor, cause the processor to carry out a method for determining a physiological parameter from one or more scalograms of a signal comprising transforming the signal using a wavelet transform to generate a transformed signal, generating a first wavelet scalogram based at least in part on the transformed signal, detecting ridges within a region of the first wavelet scalogram, determining one or more parameters for the detected ridges, determining a ridge density distribution function based at least in part on the one or more parameters, and selecting a ridge having the scale corresponding to the maximum value of the ridge density distribution function.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
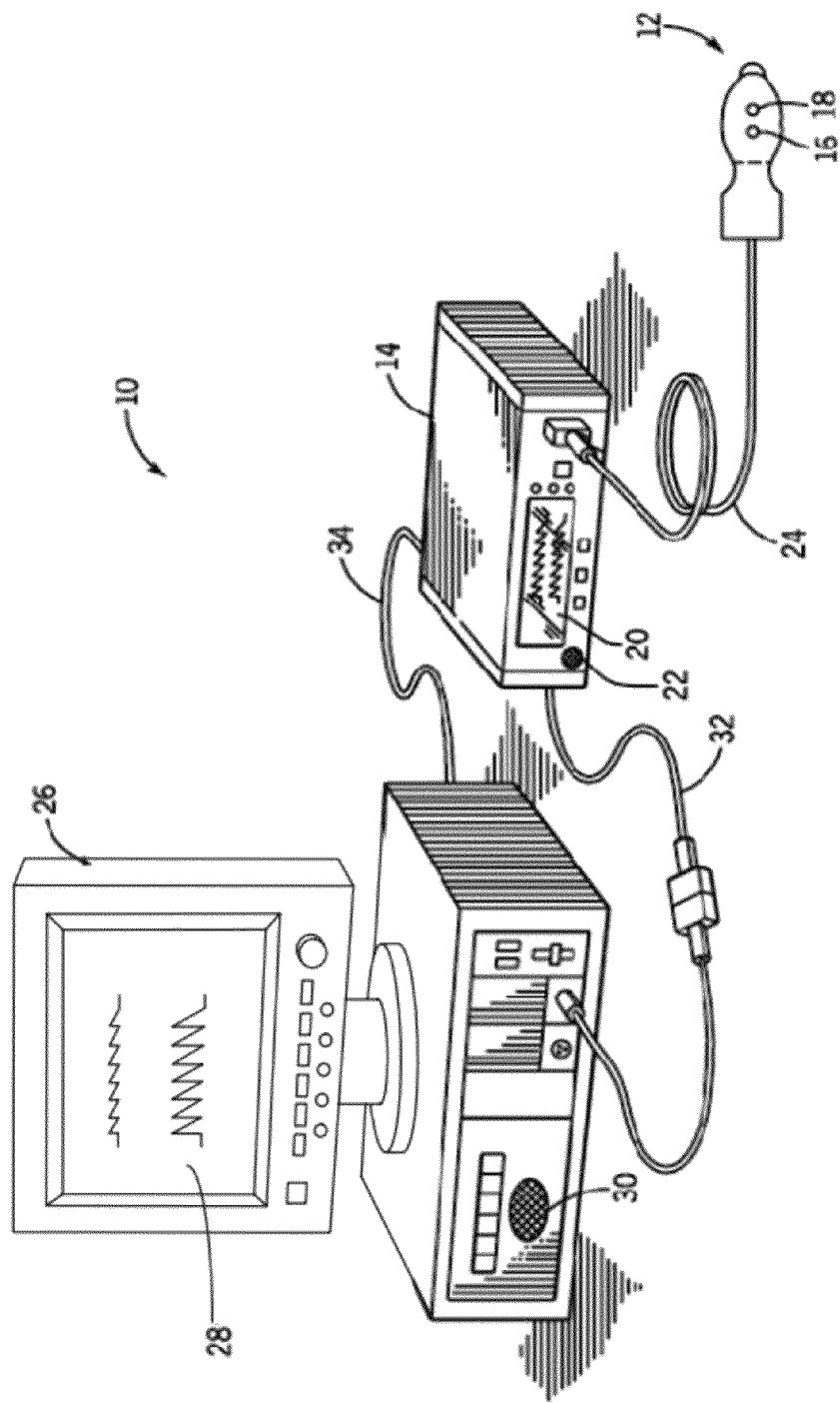
FIG. 1 shows an illustrative pulse oximetry system in accordance with an embodiment.

An oximeter is a medical device that may determine the oxygen saturation of the blood. One common type of oximeter is a pulse oximeter, which may indirectly measure the oxygen saturation of a patients blood (as opposed to measuring oxygen saturation directly by analyzing a blood sample taken from the patient) and changes in blood volume in the skin. Ancillary to the blood oxygen saturation measurement pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.
1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda,t)}{dt} \simeq \log I(\lambda,t_2) - \log I(\lambda,t_1)$$

Using log A-log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR})-\beta_r(\lambda_{IR})) - \beta_o(\lambda_R)+\beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} \quad (7)$$

$$= \frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)}$$

$$= R$$

which defines a cluster of points whose slope of y versus x will give R where $$x(t) = [I(t_2,\lambda_{IR}) - I(t_1,\lambda_{IR})]I(t_1,\lambda_R) \quad (8)$$

$$y(t) = [I(t_2,\lambda_R) - I(t_1,\lambda_R)]I(t_1,\lambda_{IR})$$

$$y(t) = Rx(t)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
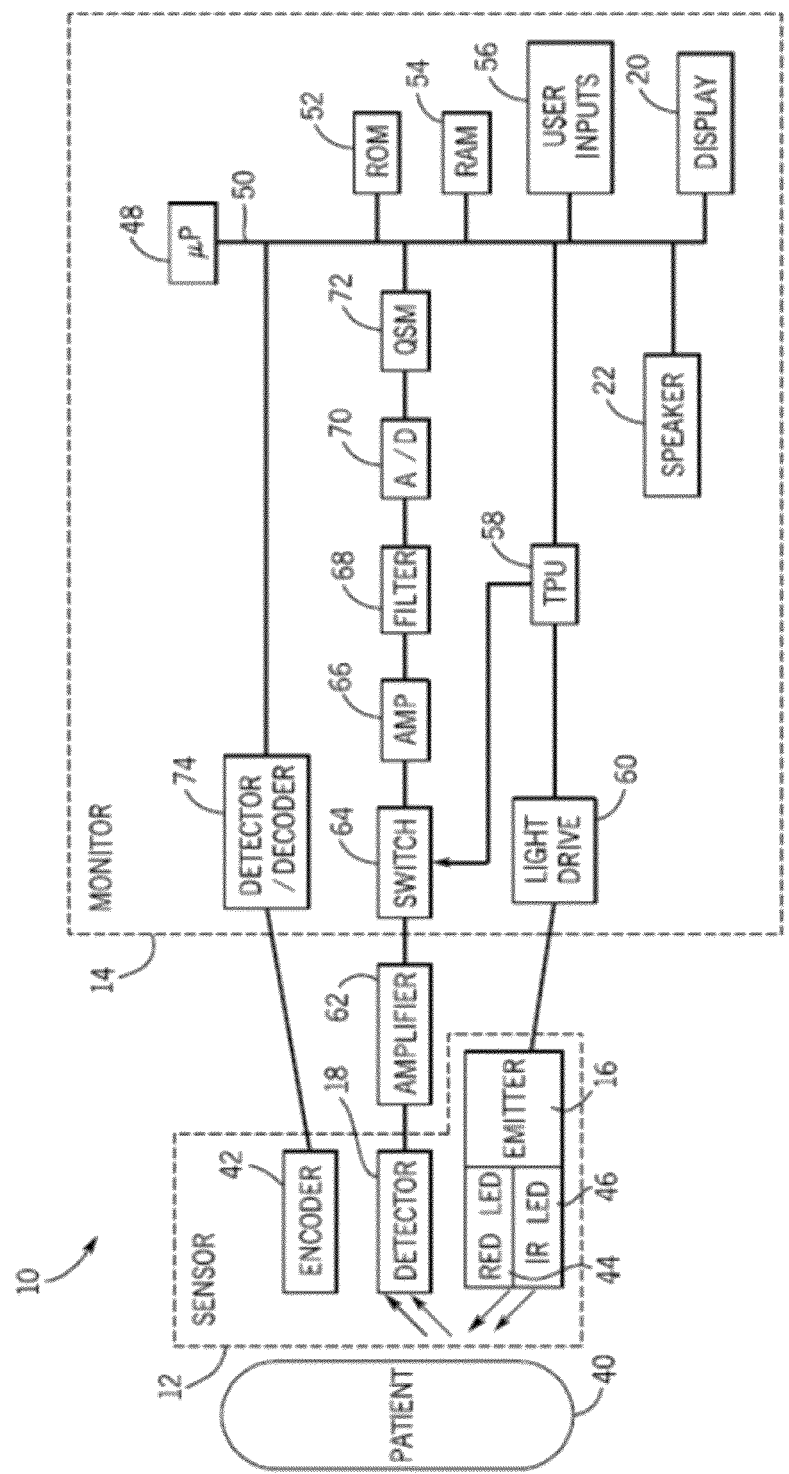
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as SpO$_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or lookup tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \qquad (9)$$

where ψ*(t) is the complex conjugate of the wavelet function ψ(t), a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e. by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \tag{10}$$

where '|| ' is the modulus operator. The scalogram may be rescaled for useful purposes. One common rescaling is defined as $$S_R(a, b) = \frac{|T(a, b)|^2}{a} \tag{11}$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \tag{12}$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{i2\pi f_0 t}-e^{-(2\pi f_0)^2/2})e^{-t^2/2} \tag{13}$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
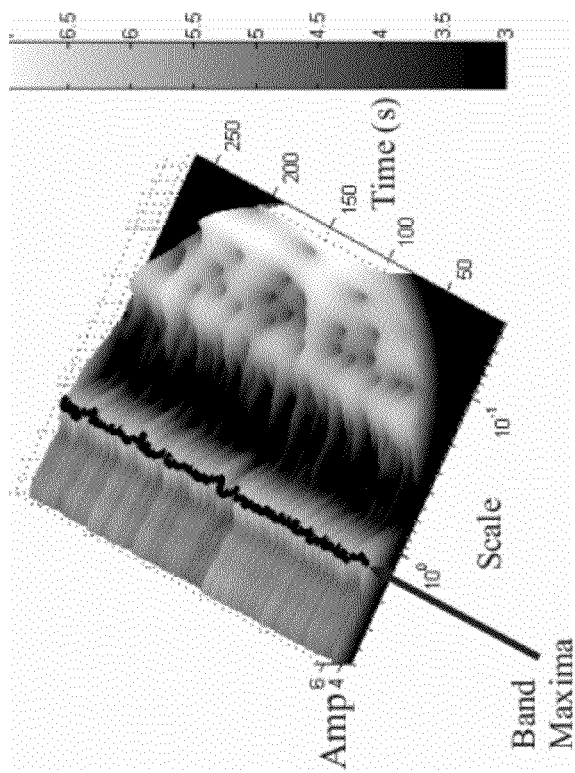
FIGS. 3(a) and 3(b) show illustrative views of a scalogram derived from a PPG signal in accordance with an embodiment.
Figure 3A:
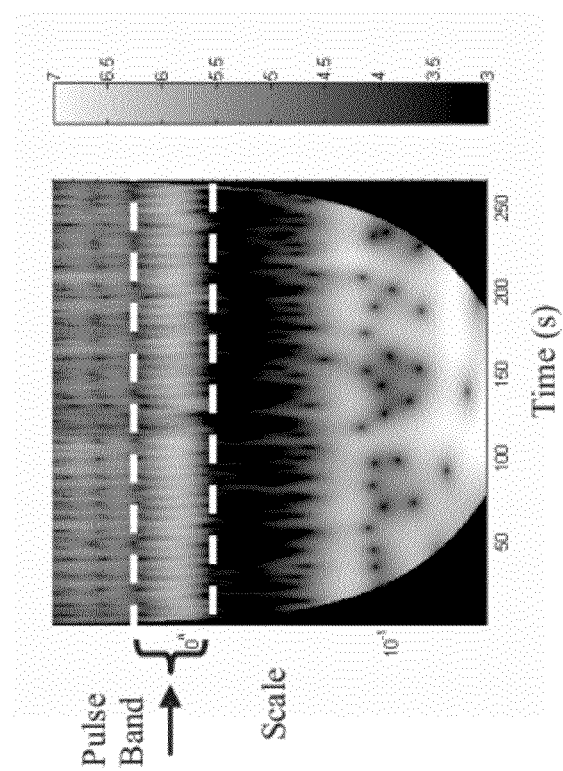

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
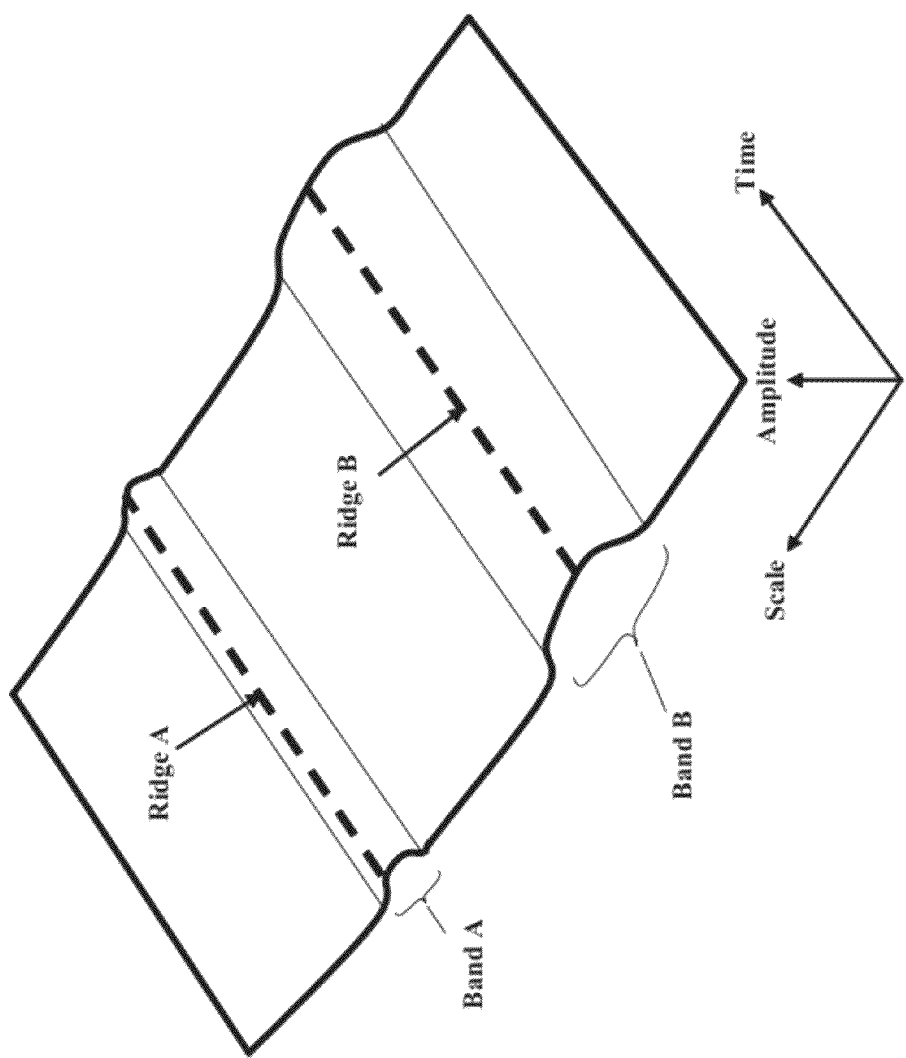
FIG. 3(c) shows an illustrative scalogram derived from a signal containing two pertinent components in accordance with an embodiment.
Figure 3D:
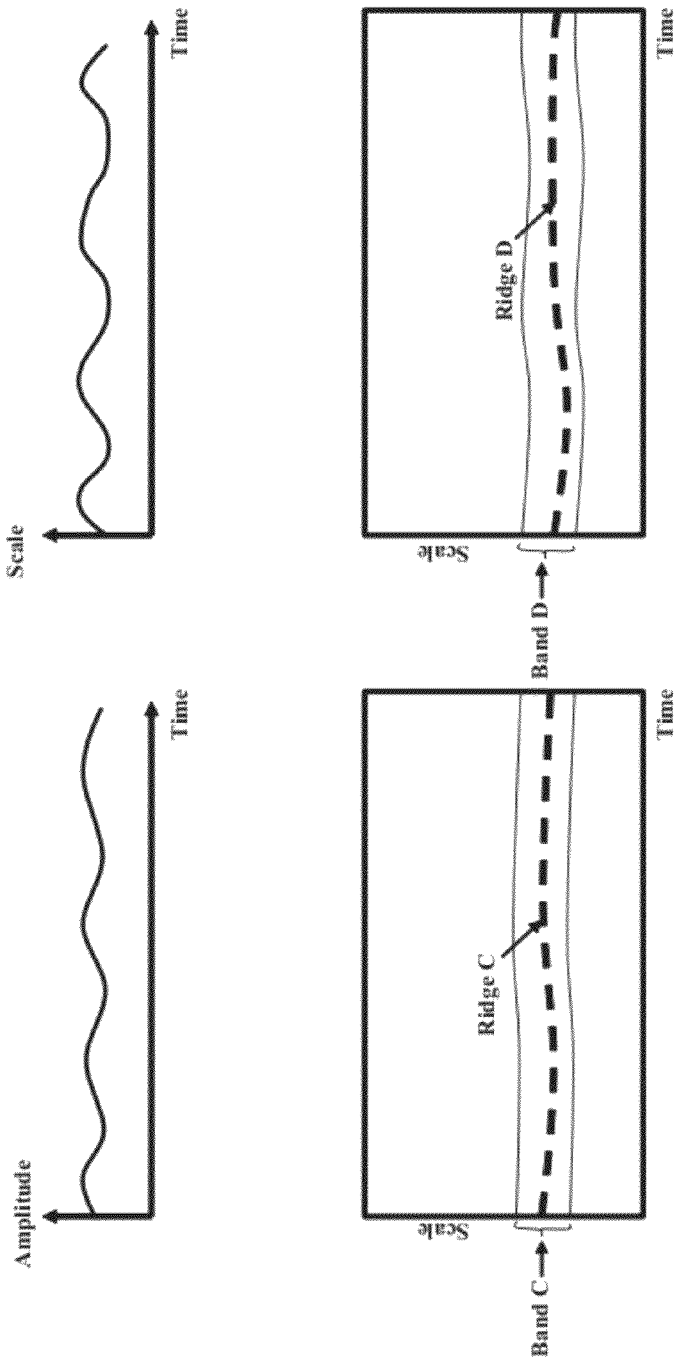
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_{0}^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_{0}^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_{0}^{\infty} \frac{|\hat{\psi}(f)|^2}{f} df \quad (17)$$

Figure 3E:
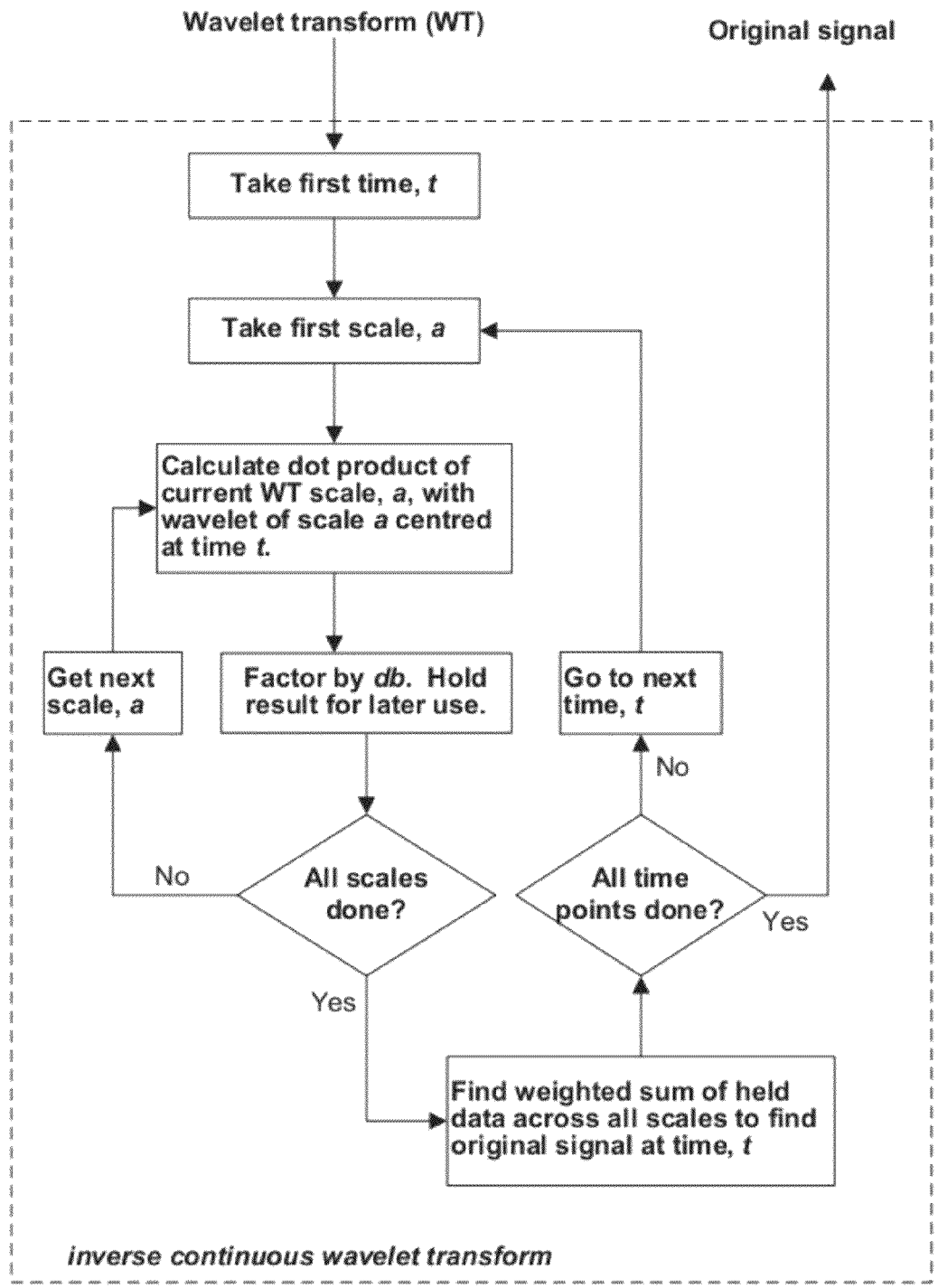
FIGS. 3(e) and 3(f) are flow charts of illustrative steps involved in performing an inverse continuous wavelet transform in accordance with embodiments.
Figure 3F:
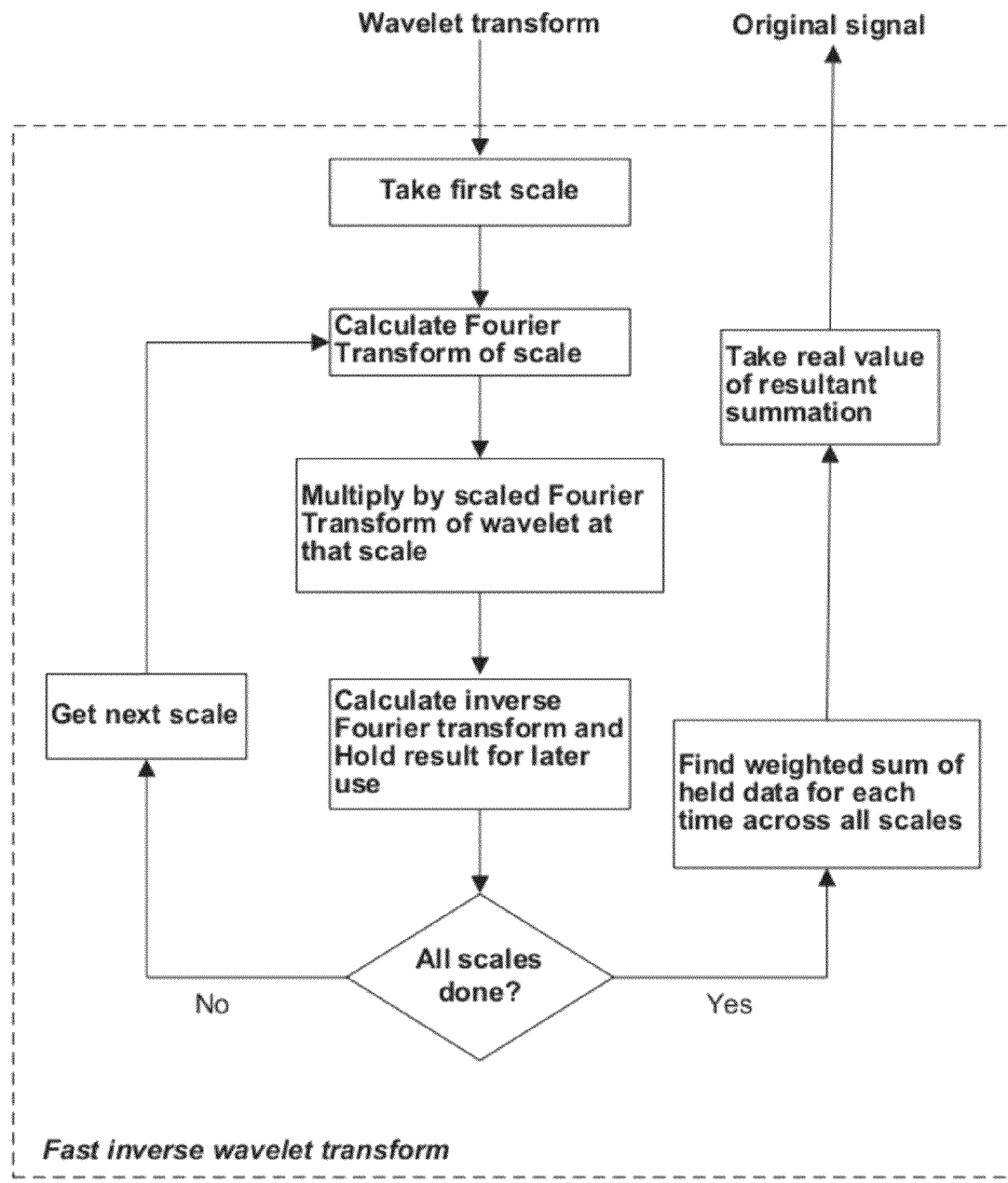

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
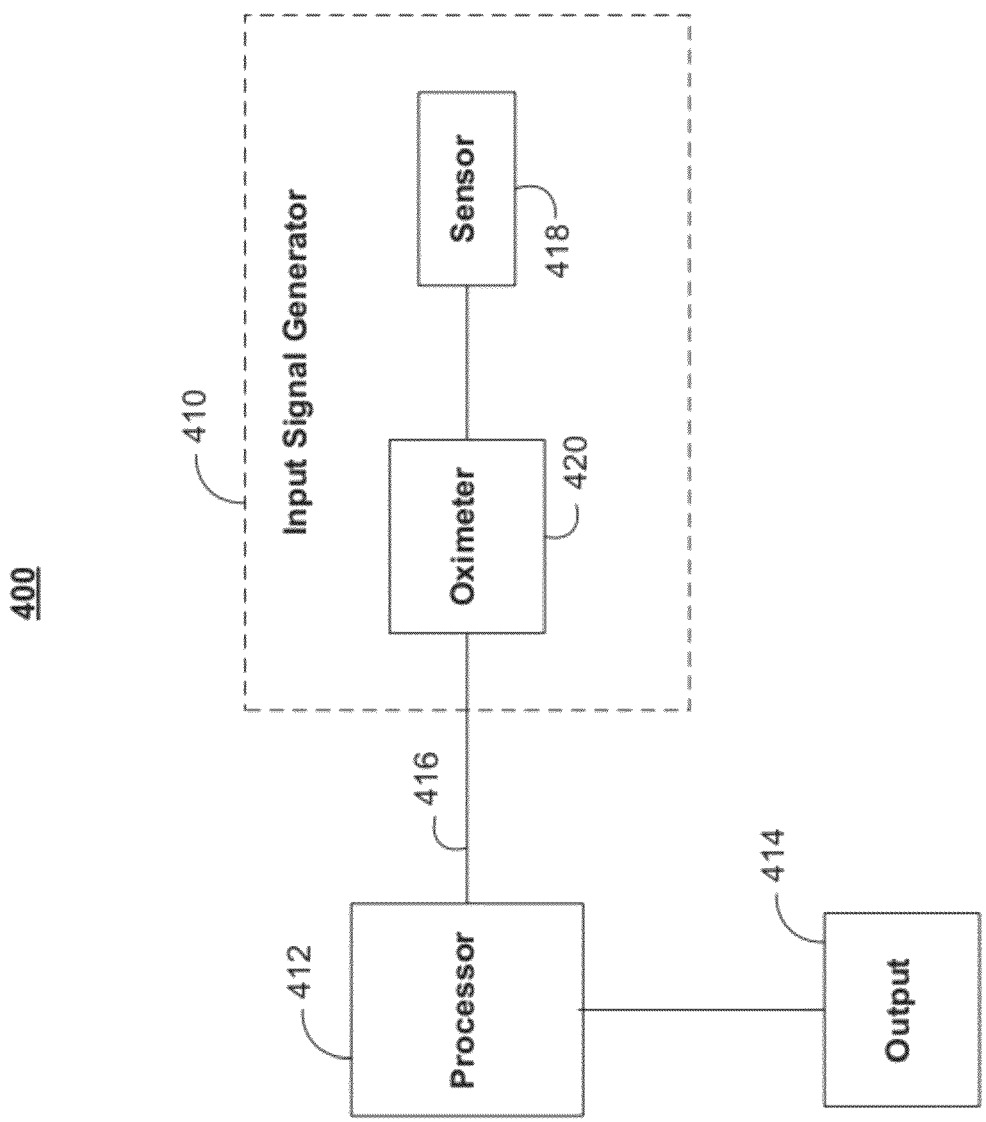
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

Figure 5A:
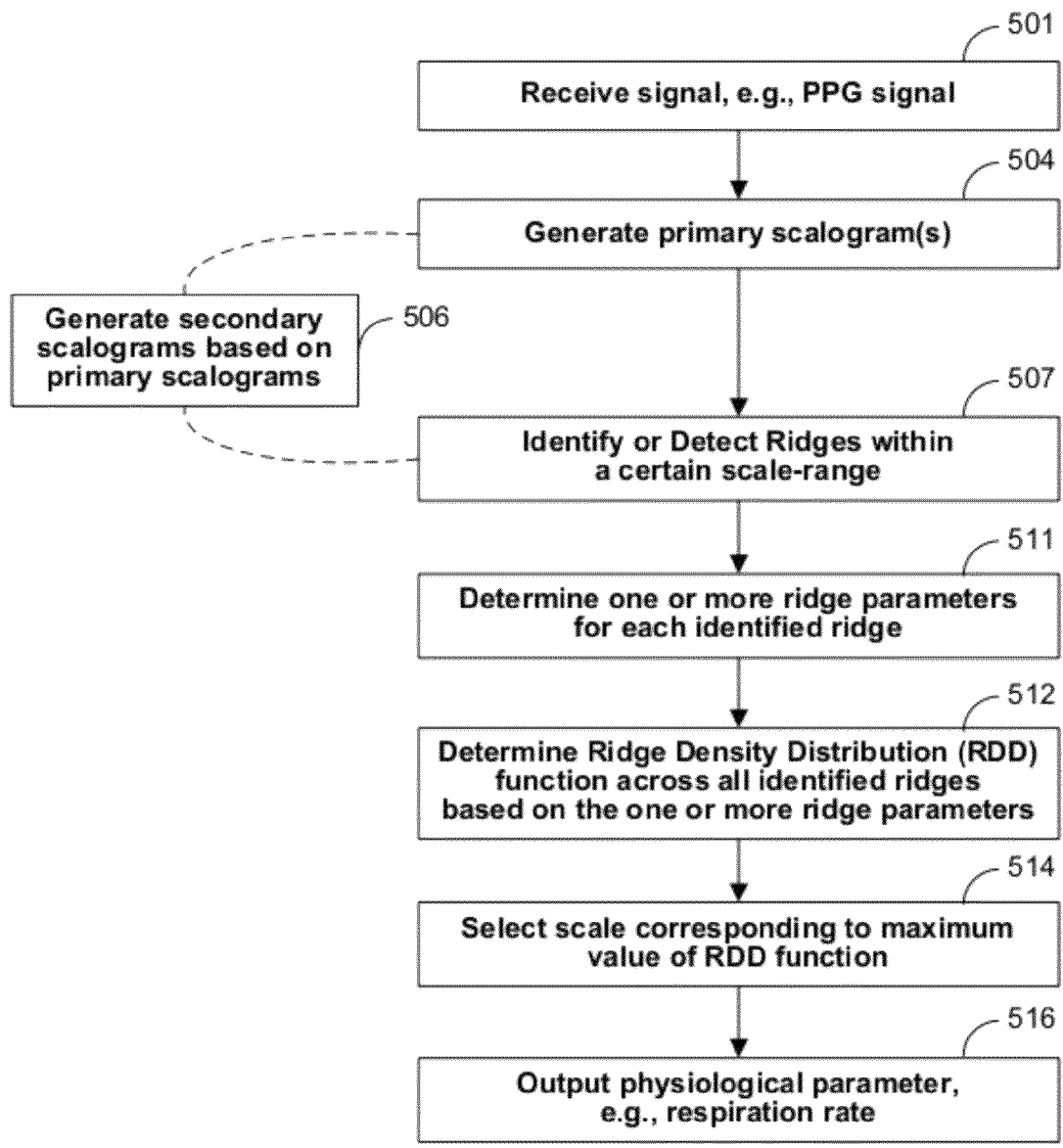
FIG. 5a is a process flow diagram for selecting ridges and determining respiration rate according to an embodiment.
Figure 5B:
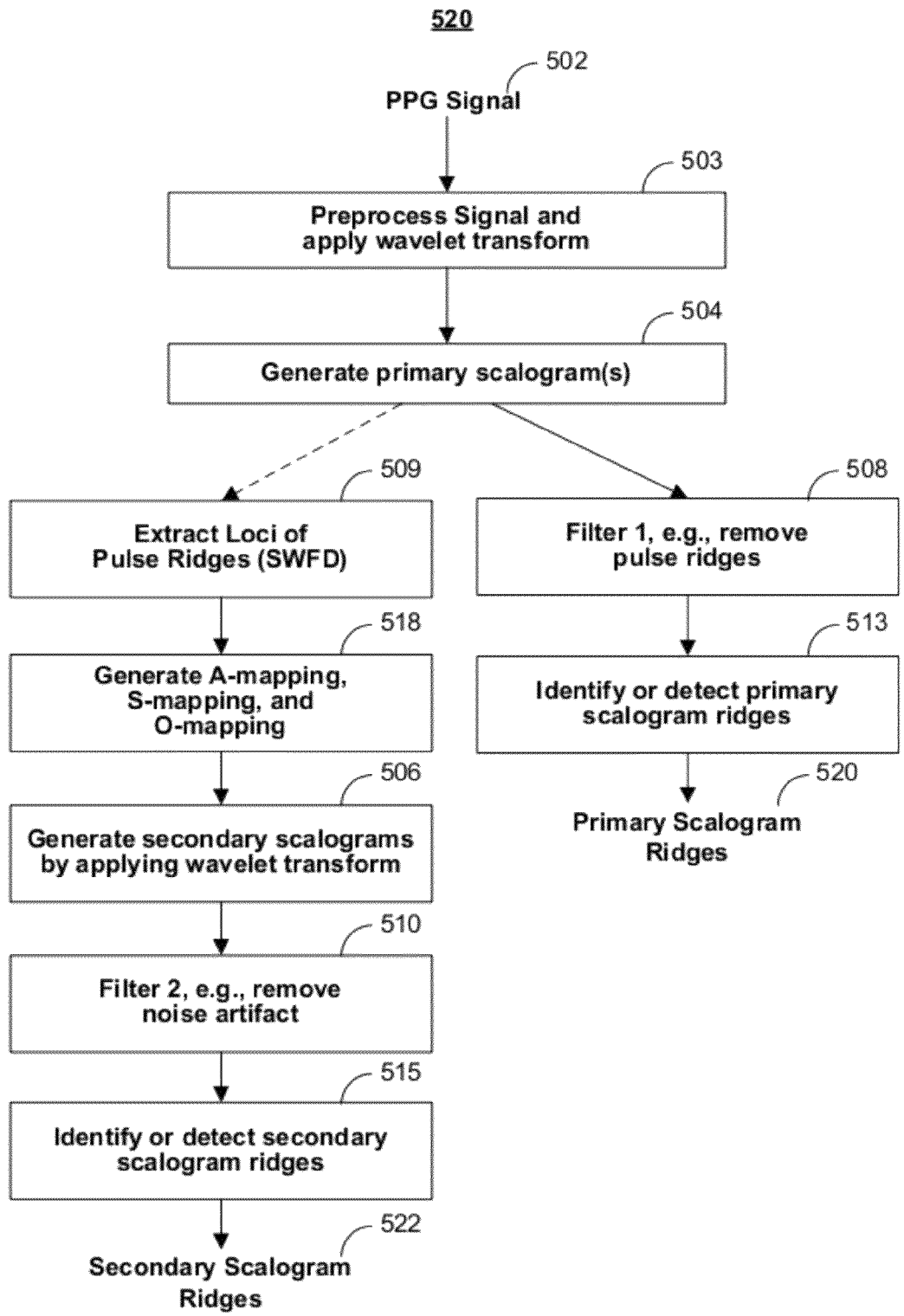
FIG. 5b is a process flow diagram for identifying ridges within one or more scalograms of a PPG signal according to an embodiment.
Figure 5C:
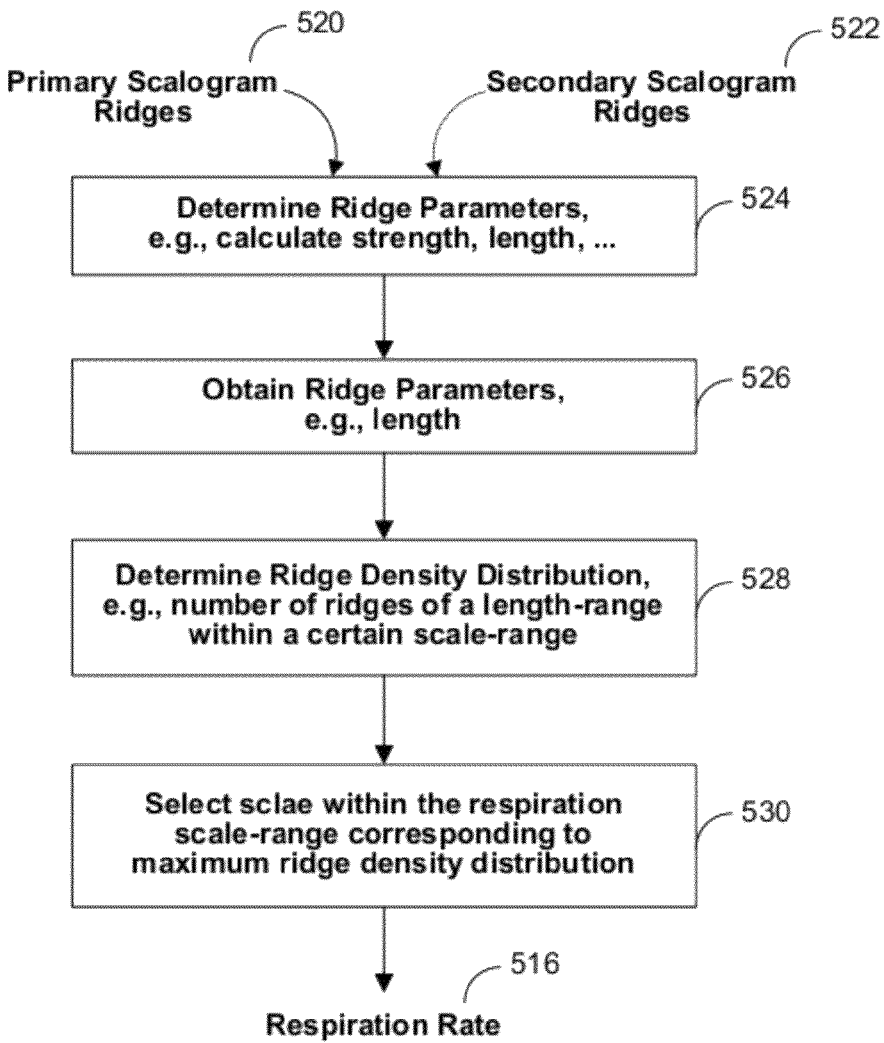
FIG. 5c is a process flow diagram for determining respiration rate using a ridge density distribution based at least in part on one or more ridge parameters according to an embodiment.
Figure 6:
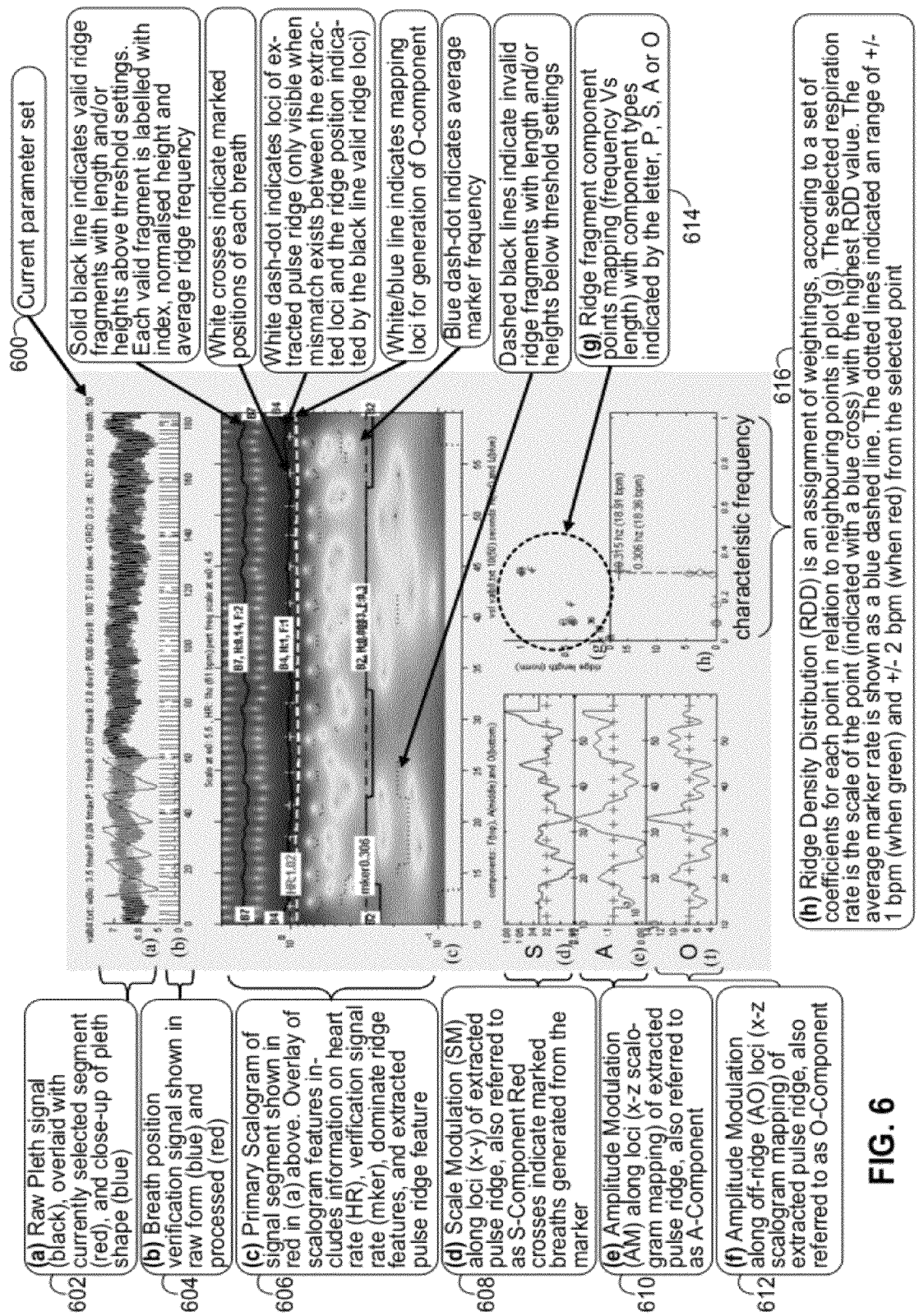
FIG. 6 is an illustration of process 500 of FIGS. 5a and 5c on a PPG signal to determine respiration rate, according to an embodiment.
Figure 7:
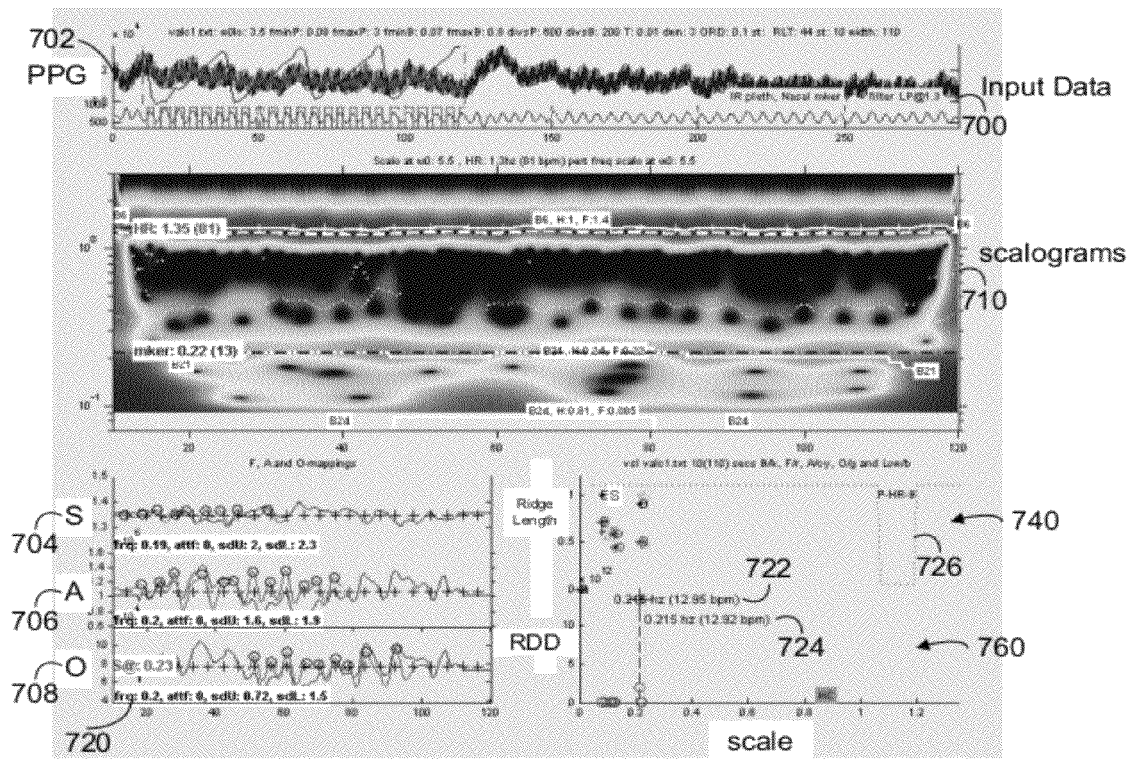
FIG. 7 shows an exemplary determination of respiration rate according to an embodiment.
Figure 8:
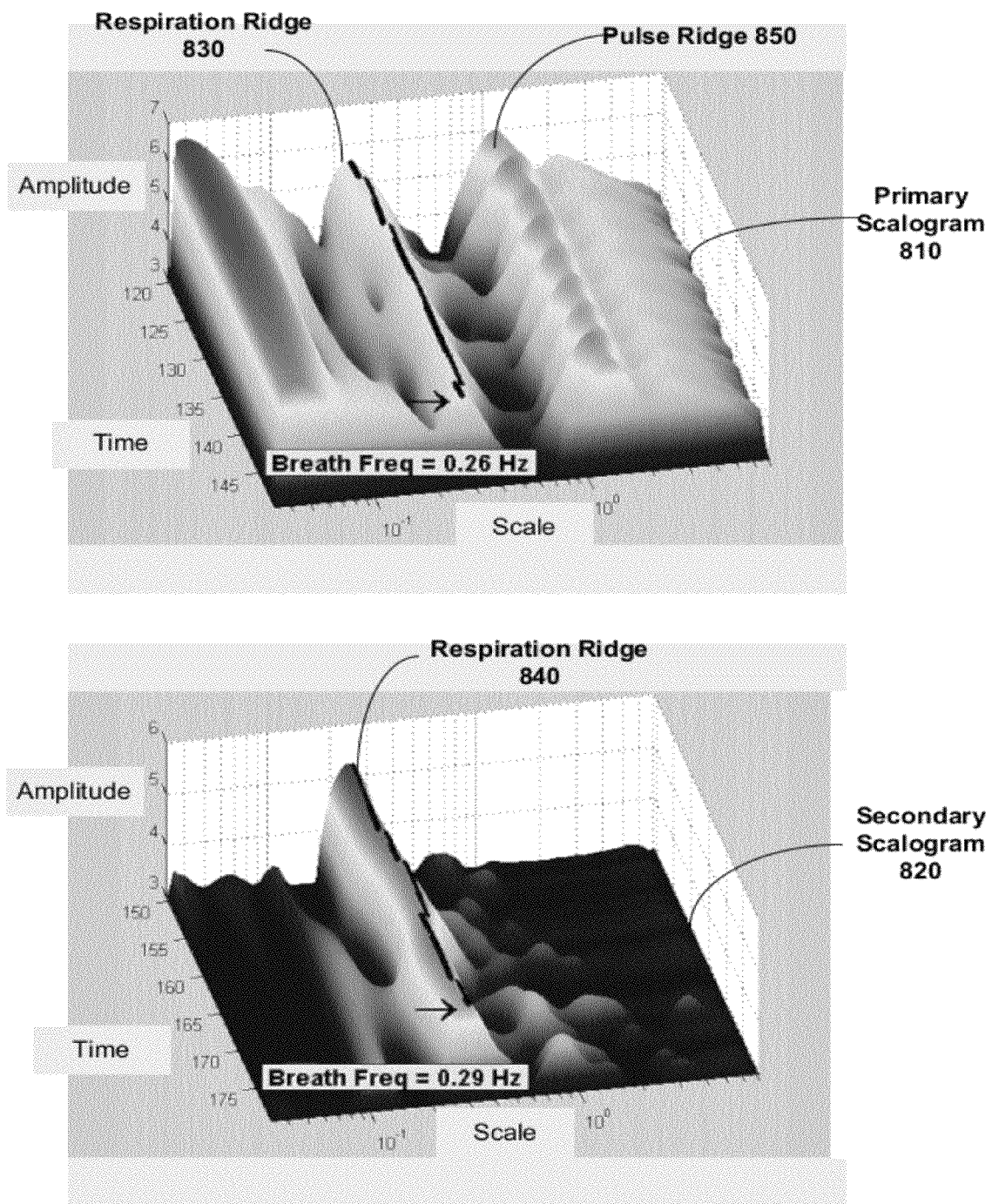
FIG. 8 is an illustration of ridges which may be analyzed according to an embodiment.
Figure 9:
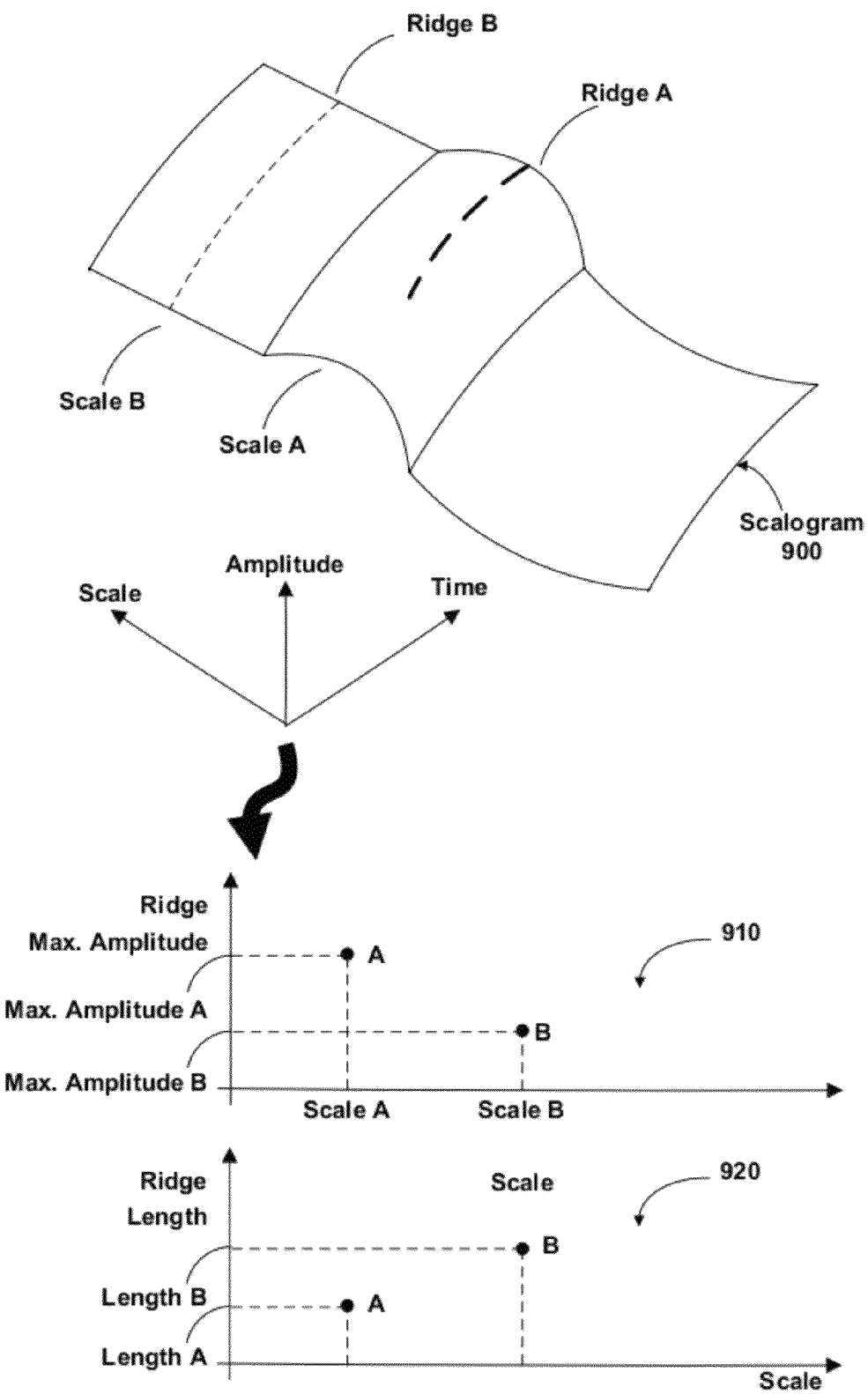
FIG. 9 is an illustration of weighting of a ridge according to an embodiment.
Figure 10:
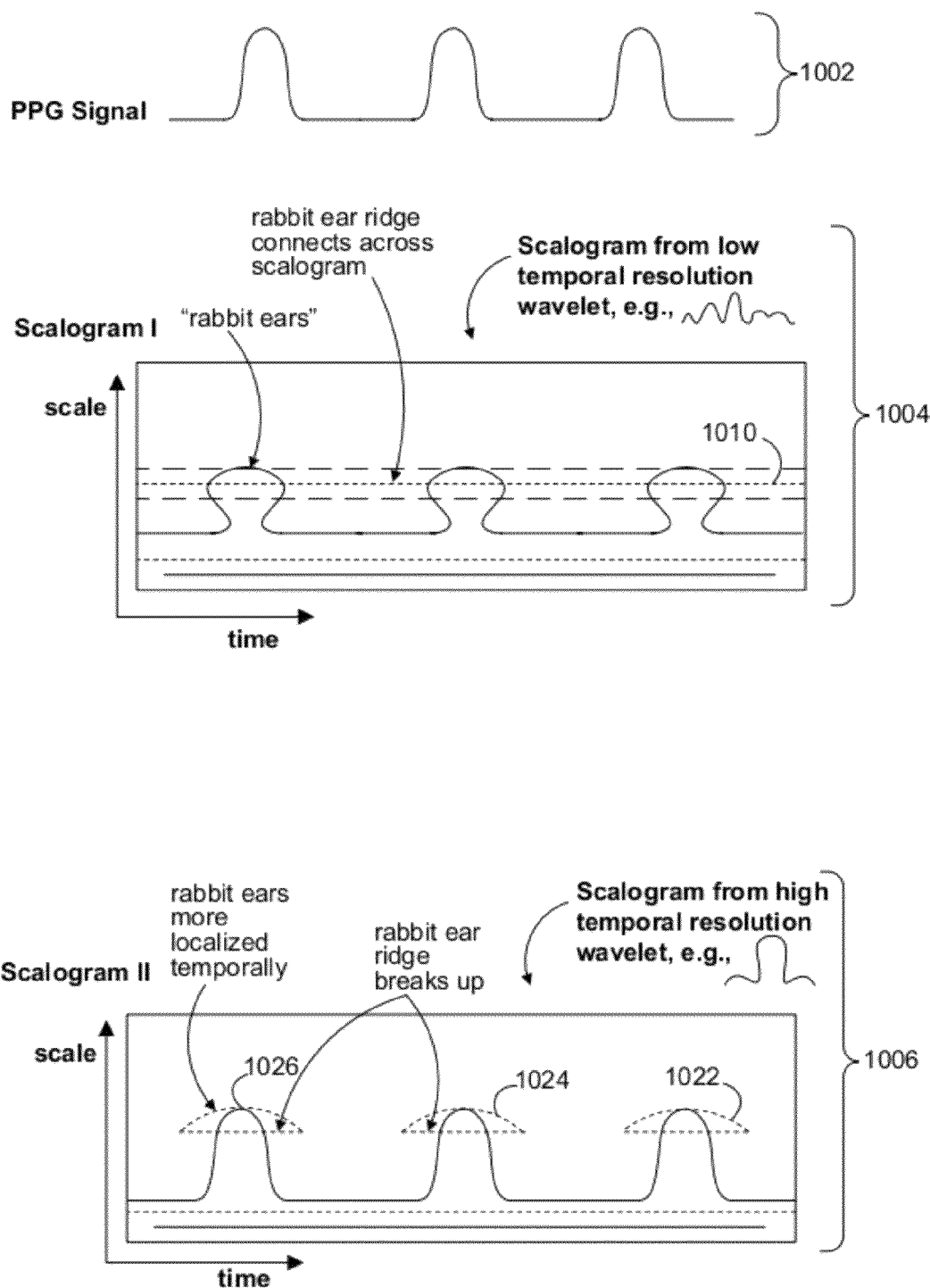
FIG. 10 is an illustration of a technique which may be used to create discontinuous ridges or "rabbit ears" according to an embodiment.

Embodiments will now be discussed in connection with FIGS. 5 through 10. In particular; systems and methods for ridge selection and determination respiration rate from one or more scalograms of a PPG signal will be discussed in detail. FIGS. 5a-c illustrate processes involved in selecting ridges and determining respiration rate from a PPG signal, while FIGS. 6 and 7 are illustrative embodiments of the processes described in FIGS. 5a-c. FIGS. 8-10 are more detailed illustrations of ridges in scalograms, and of exemplary ridge parameterizations.

FIGS. 5a-5c illustrate process flow diagrams for a method for selecting ridges and determining a physiological parameter, e.g., respiration rate, according to an embodiment. FIG. 5a shows process 500 for a signal 501 which may be executed on processor 412 of wavelet processing system 400 in FIG. 4. FIGS. 5b and 5c show process flow diagrams for determining respiration rate from a PPG signal, including the processes of identifying ridges, calculating ridge parameters, and determining a ridge density distribution function based on the determined ridge parameters, which may be executed on processor 412 of wavelet processing system 400 in FIG. 4.

In FIG. 5a, a physiological signal is received (step 501) from, e.g., a sensor such as oximeter 420 in FIG. 4, and transformed by applying a continuous wavelet transform to generate one or more primary scalograms (step 504). Primary scalograms may encompass any scalogram computed using the sensed signal 501, i.e., scalograms offset in time or offset in scale are also considered primary scalograms. As discussed above, pertinent repeating features in the signal may give rise to a time-scale band in wavelet space or in resealed wavelet space in the primary scalograms 504, or the secondary scalograms 506. In many real signals, e.g., PPG signals, these bands may be non-stationary; varying in scale, amplitude, or both over time. Optionally, secondary scalograms may be also be generated (step 506). These secondary scalograms may be generated based in part on the primary scalograms, e.g., based on a SFWD, and the signal. Ridges may then be identified or detected (step 507) and one or more ridge parameters for each identified ridge may be determined (step 511). Based on the determined ridge parameters, a ridge density distribution (RDD) function is determined (step 512). The scale corresponding to the maximum value of the RDD function is selected (step 514), and this scale is the output physiological parameter (step 516). These steps will now be described in relation to a PPG signal in the process flow diagrams of FIGS. 5b and 5c.

FIG. 5b illustrates a process flow diagram for a method for identifying primary and/or secondary ridges from a PPG signal, according to an embodiment. Physiological signal 502, e.g., a PPG signal, may be received from oximeter 420 by processor 412 of FIG. 4. In step 503, the PPG signal is pre-processed, for example, to remove noise artifacts or unwanted modulation effects. Processor 412 of FIG. 4 may compute the wavelet transform such as a continuous wavelet transform of signal 502 to obtain the primary scalogram(s) 504 of signal 502, generated according to the discussion relating to FIGS. 3(a) to 3(e) above (step 503). This primary scalogram may contain ridges in the pulse scale-range or the respiration scale-range, or in any other scale-range. For instance, the primary scalogram may contain ridges corresponding to, among others, the pulse ridge in the pulse scale-range, e.g., 1 Hz, and the respiration ridge in the respiration scale-range, e.g., 0.3 Hz. In some embodiments, only the primary scalogram is used to identify or detect ridges. The primary scalograms 504 of the signal may be filtered using filter 1 508 to remove undesired portions of the scalograms, e.g., noise artifacts or pulse ridges. Optionally, in other embodiments, the primary scalograms may be used to compute one or more secondary scalograms 506 after the pulse ridge loci are extracted (step 509). These secondary scalograms may be filtered using filter 2 510 to remove undesired portions of the scalograms, e.g., the pulse ridge or pulse band. The secondary scalograms may be based on any suitable mapping of the primary scalogram, e.g., SWFD, that results in a secondary signal (step 518). Examples of SWFDs include a signal that is obtained from a time-scale mapping along the extracted pulse ridge loci (illustrated in Graph 608 as will be explained below in relation to FIG. 6), also referred to as an S-mapping or S component or the Scale Modulation (SM) ridge component, which is an example of an RSP signal, a time-energy or time-scalogram amplitude mapping along the extracted pulse ridge loci (illustrated in Graph 610 as will be explained in relation to FIG. 6), also known as an A-mapping or A component or the Amplitude Modulation (AM) ridge component, or a time-energy or time-scalogram amplitude mapping at a locus of points equally offset from the extracted pulse ridge loci (illustrated in Graph 612 as will be explained in relation to FIG. 6), also known as an O-mapping or O component Continuous wavelet transforms of the O-mapping, S-mapping, and A-mapping, may be computed (step 506), and these transforms are referred to as secondary scalograms. These secondary scalograms may contain ridge components corresponding to the respiration scale-range. Although the secondary scalograms are discussed as corresponding to the A-mapping, S-mapping, and O-mapping, any other suitable secondary scalogram may be used. Note that the primary and secondary scalograms can be computed using a predetermined time period within the signal 504 and the primary scalograms 504, e.g., a five-second time period or any other suitable time period. In some embodiments, a moving time period or window may be used to perform the scalogram computations. The secondary scalograms may be filtered, for example, to remove noise or unwanted components, with filter 2 510 (or a second wavelet scalogram mask).

Once the primary, and in some embodiments, secondary scalograms, have been computed, processor 412 of FIG. 4 may detect and identify ridges within these scalograms in the respiration scale-range (steps 513 and/or 515). Such an identification or detection may be performed by selecting ridges that are within an acceptable breath frequency, e.g. 12-18 breaths per minute, or 0.2-0.3 Hz. Any suitable identification method may be used to select ridges within the respiration scale range. The output of the identification process are a set of primary scalogram ridges 520, and a set of secondary scalogram ridges 522.

FIG. 5c illustrates a process flow diagram for determining respiration rate from the set of primary scalogram ridges 520, and a set of secondary scalogram ridges 522 in FIG. 5b, according to an embodiment. In particular, FIG. 5c is a process flow diagram 550 for calculating and deriving a ridge density distribution from the primary and/or secondary scalogram ridges based on the selected ridge parameters. In one embodiment, the primary scalogram ridges 520 are parameterized, i.e., parameters that characterize these ridges are calculated and/or derived. Optionally, in other embodiments, both the primary scalogram ridges 520 and the secondary scalogram ridges 522 are parameterized (step 524). Examples of such parameters include ridge strength, ridge length, ridge power (power is the rate of transfer of energy), ridge energy, ridge energy density (energy density is the amount of energy per unit area of the transform surface, which may be thought of as a surface discretized into a patchwork of tiles each of which has an associated energy), ridge amplitude, ridge amplitude variability, ridge scale variability, ridge consistency, product of ridge strength and ridge length, the intrinsic or characteristic scale for the ridge. In some embodiments, the ridges 520 and 522 may be characterized in terms of products of or weighted sums of these parameters (step 526). In other embodiments, ridges 520 and 522 may be characterized in terms of only one of these parameters (step 526). Based on the calculated/derived ridge parameters, at step 528, a ridge density distribution or ridge density distribution function, e.g., ridge parameters or a weighting of ridge parameters as a function of scale, may be calculated (step 528). For example, the total length of ridges as a function of scale, or the total energy of ridges as a function of scale. In preferred embodiments, respiration rate 516 may be determined as being the scale within the respiration scale-range corresponding to the maximum value of the ridge density distribution (step 530).

Ridge density distribution (RDD) as generated, for example, in step 528 of FIG. 5c, may be calculated in any suitable manner. For example, ridge density distribution may be computed as a histogram of ridges of a certain length for a given scale (see for example, Graph 616 in FIG. 6 or Graph 1060 in FIG. 10). In other embodiments, ridge density distribution may be computed as a histogram of ridges of a certain strength for a given scale. In some embodiments, the ridge parameters may be weighted using any suitable weighting. Such a weighting may be achieved by any suitable ridge density distribution (RDD).

In some embodiments, an RDD includes an assignment of weightings, or a mapping of ridge parameters to weighted ridge parameters, based on a set of weighting coefficients for each ridge in relation to neighboring (in the scale axis) ridges, see, e.g., the discussion accompanying FIG. 9. The goal in such weighting may be to reduce the relative importance of some ridge components, which may be useful when attempting to remove ridge components which are not of interest. In other embodiments, some characterizing parameters or weighting parameters are considered more important than others, e.g., length, strength-length product, or any other suitable parameter, may be considered to be of more significance than other parameters.

In embodiments, the weighting of a ridge may be decreased based on characterizing parameter values. For example, a ridge with high amplitude or scale variation may cause a ridge to have a lower weighting than one with low amplitude or scale variation. Ridges may also be weighted based on a comparison of characterizing parameters of the ridge being weighted relative to the characterizing parameter(s) of other ridges. For example, a first ridge having parameters that are similar to the parameters of second ridge (e.g., scale, length, and amplitude) may cause the weighting of the first ridge to increase. This may cause respiration ridges from different scalograms to have a reinforcing or multiplying affect on each other. In some embodiments, the respiration rate that is selected is the scale at the point with the maximum RDD value i.e. respiration rate is the scale within the respiration scale-range at which the largest density of ridges occurs.

Turning now to FIG. 6, an illustration of how process 500 of FIG. 5 may be applied to a PPG signal to determine respiration rate is shown. Graph 602 shows a PPG signal with a segment which is under analysis, and a close-up of the modulation of the PPG signal below this segment. A breath position verification signal in raw form and processed form corresponding to this PPG signal appears in Graph 604. Graph 606 shows the primary scalogram of a portion of the red segment of the PPG signal segment being analyzed. This scalogram shows several dominant ridge features, including, but not limited to, pulse ridges (corresponding to heart rate) in the pulse scale-range and respiration ridges in the respiration scale-range. In preferred embodiments, the pulse ridges may be extracted (see, e.g., extracted pulse ridges 509 in process 500 of FIG. 5*a*). Graphs 608, 610, and 612 show features extracted from the primary scalogram that may be used to generate secondary scalograms. Specifically, graph 608 shows scale modulation of the extracted pulse ridge in Graph 606 along the ridge loci. Graph 610 shows amplitude modulation of the extracted pulse ridge in Graph 606 along the ridge loci. Graph 612 shows off-ridge amplitude modulation of the extracted pulse ridge in Graph 606 along the ridge loci. Graphs 614 and 616 show how respiration rate may be determined from the RDD, as explained in more detail in relation to FIGS. 7-10. In particular, the ridges obtained from the primary and secondary scalograms in the respiration scale-range may be characterized in terms of their length. Graph 616 shows a plot of ridge length versus scale, with each point representing a different ridge at a specific scale. In some embodiments, the respiration rate is selected as the scale at the point with the highest RDD value i.e. respiration rate is the scale within the respiration scale-range at which the largest density of ridges occurs. In some embodiments, the ridge density distribution may be filtered, e.g., with a notch filter, to remove undesired scale-ranges e.g., ranges of scale corresponding to pulse rate. For example, in FIG. 6, respiration rate, i.e., 0.315 Hz, is determined by selecting the scale at which the ridge distribution density is maximum in Graph 616.

In some embodiments, the RDD may include an assignment of weightings according to a set of coefficients for each point in relation to neighboring points. For instance, points which are grouped together may receive a higher weighting than points which lie apart from groups. To this end, closer-grouped points re-enforce each other, while points spaced far apart or isolated points do not get re-enforced. For example, the RDD in graph 616 in FIG. 6 may be based in part on relationships between points in graph 614 in FIG. 6. Such a weighting may be performed, among others, using a nearest neighbors analysis method.

FIG. 7 shows another exemplary respiration rate determination according to an embodiment. A physiological signal 702, e.g., a PPG signal, may be analyzed and processed as part of input data 700 to produce one or more primary scalograms 710. S, A, and O components 704, 706, and 708, respectively, may be derived from the primary scalogram and used to generate secondary scalograms. The S, A, and O components are displayed in composite graph 720. Ridges may be identified in one, several, or all of the generated scalograms. The identified ridges may be shown, for example, in graph 740, which plots normalized ridged length against a scale parameter of ridges. Graph 740 also illustrates the use of a notch filter 726 to remove undesired scales in the ridge length-frequency plot. The scales removed using notch filter 726 may be identified using the filtering techniques discussed above in relation to FIG. 6.

Graph 760 in FIG. 7 is a plot of the Ridge Density Distribution (RDD) versus scale, according to an embodiment. The RDD value for a ridge may be its weighting based on one or more ridge parameters or other weighting parameters. In some embodiments, the RDD may be based on a decision tree in which a weighted branching is used. This weighted branching may be based on, among others, an inter-ridge relationship between ridge components (e.g., the degree of cohesion between ridges, the degree of correlation between ridges, or any other suitable inter-ridge relationship) and parameters characterizing the ridges themselves (e.g., the start and end positions of the ridges, the ridge lengths, variance of ridge energy, ridge entropy, or any other suitable parameter). In an embodiment, the ridge having the highest RDD weighting may be representative of respiration rate. As shown in graph 760 in FIG. 7, the ridge having the highest RDD weighting (i.e., RDD 722) may correlate to a respiration rate of approximately 13 breaths per minute. The respiration rate may be determined based on the characteristic frequency of the scale of the highest weighted ridge or using any other suitable mapping.

As shown in graph 760, another RDD 724 is shown to be close to RDD 722, according to an embodiment. This may occur when two or more continuous respiration ridges are identified on two or more scalograms. When multiple ridges are determined to have high weightings, the highest weighted ridge may be selected for determining respiration rate. Alternatively, a weighted average, median, or other suitable measurement of the two or more highest weighted ridges may be used to determine respiration rate or any other suitable parameter.

FIG. 8 is an illustration of scalograms of a PPG signal that may be analyzed according to an illustrative embodiment. The top portion of FIG. 8 illustrates a primary scalogram 810 of a PPG signal in which a respiration ridge 830 is highlighted. This ridge corresponds to a respiration frequency of 0.26 Hz. Also shown in the primary scalogram 810 of FIG. 8 is a pulse ridge 850 corresponding to heart rate. The primary scalogram 810 is one that may be computed at step 504 of process 500 in FIG. 5*a*. Ridges such as ridge 830 or ridge 850 which are ridges in the primary scalogram may be referred to as B components.

The bottom portion of FIG. 8 corresponds to a secondary scalogram 820 that may be obtained by computing the continuous wavelet transform of a signal derived from primary scalogram 810. The secondary scalogram 820 is one that may be computed at step 506 of process 500 in FIG. 5*a*. Continuous wavelet transforms of the O-mapping, S-mapping, and A-mapping, may be computed as described above in relation to FIG. 5*b*, and these transforms may be referred to as secondary scalograms. Although the secondary scalograms discussed herein correspond to the A-mapping, S-mapping, and O-mapping, any other suitable secondary scalogram may be used. The respiration ridge 840 in secondary scalogram 820 corresponds to a respiration frequency of 0.29 Hz. As shown in FIG. 8, secondary scalogram 820 may not have a ridge corresponding to heart rate when it is derived from the pulse ridge.

In some embodiments, ridges may be parameterized in terms of one or more quantities which characterize the ridge, as illustrated in graph 614 in FIG. 6 or in FIG. 9, or in terms of quantities or variables which characterize the relationship between two or more ridges. In one embodiment, the ridges may be represented by one quantity. For example, a ridge may be represented by its mean amplitude. In FIG. 9, such a parameterization may be carried out for ridges A and B in scalogram 900 based on maximum amplitude (parameterization 910) and ridge length (parameterization 920). Also, in FIG. 6, such a parameterization may be carried out based on ridge length in Graph 614. Note that different parameterizations may characterize the ridge components in different ways. For example, the relative strength of ridge A or ridge B may appear to be different depending on which parameterization is used. See, for example, the relative properties of ridges A and B in parameterizations 910 and 920, respectively, in FIG. 9.

In some embodiments, before calculating parameters for the ridges or even before identifying the ridges, filtering may be performed to remove undesired information as described in relation to FIG. 5a-c above. For example, it is possible that any of the scalograms described herein may suffer from a high degree of cohesion, i.e., a high degree of time-scale overlap between ridge components. Inasmuch as this overlap may obscure desired information, e.g., a ridge corresponding to respiration rate, from undesired information, e.g., noise or movement artifacts, or a ridge corresponding to the pulse rate, the filters described in relation to FIGS. 5a-c may be employed to remove the undesired information, e.g., identify bands or features that may occur due to artifacts, noise, or other phenomena. The filtering process may, for example, generate a mask to ignore regions of the scalogram. Alternatively, the filtering process may zero-out the amplitude in regions of the scalogram. The filtering process may use techniques described in Addison et al. U.S. patent application Ser. No. 12/245,232, filed Oct. 3, 2008, entitled "Methods and Systems for Discriminating Bands in Scalograms," which is incorporated by reference herein in its entirety. In the discussion herein, it may be assumed that that the filtering process has been performed. However, the discussion is also applicable if no filtering has been performed.

The type of wavelet used to compute a scalogram may affect the relative properties of a parameterized ridge and its corresponding band as illustrated in an embodiment in FIG. 10. In FIG. 10, a technique is shown that may be used to minimize the effect of "rabbit ears" according to an embodiment. Rabbit ears are a phenomena that may occur on bands within a scalogram, mainly due to differences in the temporal resolution of the wavelets used to obtain the scalogram. In particular, scalograms created by computing continuous wavelet transforms of the signal at different temporal resolutions, e.g., a low-temporal wavelet (i.e., a more oscillatory wavelet) may be used to compute one scalogram of the signal, while a high-temporal wavelet (i.e., a less oscillatory wavelet) may be used to compute another scalogram of the signal, may result in remarkably different ridges. In FIG. 10, a physiological signal 1002, e.g., a PPG signal may be used to compute two scalograms: scalogram I 1004 and scalogram II 1006. In scalogram 1004, a low temporal resolution wavelet may be used, which may cause relatively large rabbit ears to occur. The rabbit ears may connect to create a ridge 1010 spaced apart from the ridge of the band (e.g., respiration band) from which they extend. The ridge running through the rabbit ears may not be a ridge of interest. In scalogram 1006, a higher temporal resolution wavelet may be used to generate a scalogram where effects of the rabbit ears may be minimized. As shown in FIG. 10, rabbit ears ridge 1010 from scalogram 1004 may be broken into three ridge segments 1022, 1024, and 1026 when a higher temporal wavelet is used in scalogram 1006. Accordingly, when ridges identified from 1004 and 1006 are analyzed and weighted, the ridges corresponding to the bands in scalograms 1004 and 1006, which are similar to each other, may reinforce each other and be weighted higher than the rabbit ears ridges, which may be of different sizes and amplitudes between the two scalograms. However, it should be noted that using wavelets of too high of a resolution may also cause the ridge of the respiration band or other bands of interest to break into separate ridge segments, which may not be desirable.

The foregoing is merely illustrative of the principles of this disclosure and various modifications can be made by those skilled in the art without departing from the scope and spirit of the disclosure. The following numbered paragraphs may also describe various aspects of this disclosure.

What is claimed is:

1. A method comprising:
   transforming a signal based at least in part on a wavelet transform to generate a transformed signal,
   generating a first wavelet scalogram based at least in part on the transformed signal,
   detecting ridges within a region of the first wavelet scalogram,
   determining one or more parameters for the detected ridges,
   determining a ridge density distribution function based at least in part on the one or more parameters, and
   selecting a ridge based at least in part on the ridge having a scale corresponding to a maximum value of the ridge density distribution function.

2. The method of claim 1, wherein the signal is a photoplethysmographic signal.

3. The method of claim 1, further comprising filtering the first wavelet scalogram.

4. The method of claim 1, further comprising generating a second wavelet scalogram based at least in part on a signal derived from the first wavelet scalogram and detecting ridges within a region of the second wavelet scalogram.

5. The method of claim 1, wherein the parameters of the detected ridges comprise ridge power, ridge energy, ridge energy density, ridge amplitude variability, ridge scale variability, ridge consistency, intrinsic scale, ridge length, maximum ridge amplitude, standard deviation of intrinsic scale, standard deviation of amplitude, mean scale, median scale, mean amplitude, median amplitude, and/or strength-length product.

6. The method of claim 1, further comprising determining a physiological parameter based at least in part on the selected ridge.

7. The method of claim 6, wherein the physiological parameter comprises respiration rate.

8. A computer-readable medium comprising computer-executable instructions which, if executed by a processor, cause the processor to carry out a method for determining a physiological parameter from one or more scalograms of a signal comprising:
   transforming an input signal at least in part on using a wavelet transform to generate a transformed signal,
   generating a first wavelet scalogram based at least in part on the transformed signal,
   detecting ridges within a region of the first wavelet scalogram,
   determining one or more parameters for the detected ridges,
   determining a ridge density distribution function based at least in part on the one or more parameters, and selecting a ridge based at least in part on the ridge having a scale corresponding to a maximum value of the ridge density distribution function.

9. The computer-readable medium of claim 8, wherein the signal is a photoplethysmographic signal.

10. The computer-readable medium of claim 8, further comprising computer-executable instructions which, if executed by a processor, cause the processor to generate a second wavelet scalogram based at least in part on a signal derived from the first wavelet scalogram and detect ridges within a region of the second wavelet scalogram.

11. The computer-readable medium of claim 8, wherein the parameters of the detected ridges comprise ridge power, ridge energy, ridge energy density, ridge amplitude variability, ridge scale variability, ridge consistency, intrinsic scale, ridge length, maximum ridge amplitude, standard deviation of intrinsic scale, standard deviation of amplitude, mean scale, median scale, mean amplitude, median amplitude, and/or strength-length product.

12. The computer-readable medium of claim 8, further comprising computer-executable instructions which, if executed by a processor, cause the processor to determine a physiological parameter based on the selected ridge.

13. The computer-readable medium of claim 12, wherein the physiological parameter comprises respiration rate.

14. The method of claim 1, wherein the ridge density distribution function is calculated as a histogram of the one or more parameters for a given scale.

15. The method of claim 1, wherein the ridge density distribution is at least partially based on a set of weighting coefficients for each ridge.

16. The method of claim 8, wherein the ridge density distribution function is calculated as a histogram of the one or more parameters for a given scale.

17. The method of claim 8, wherein the ridge density distribution is at least partially based on a set of weighting coefficients for each ridge.

* * * * *